United States Patent
Wei et al.

(10) Patent No.: US 7,823,163 B2
(45) Date of Patent: *Oct. 26, 2010

(54) METHODS AND SYSTEM FOR PROCESS SHARING AMONG INDEPENDENT SYSTEMS/APPLICATIONS VIA DATA ENCAPSULATION IN MEDICAL IMAGING

(75) Inventors: Guo-Qing Wei, Plainsboro, NJ (US); Cheng-Chung Liang, West Windsor, NJ (US); Feng Ma, Pennington, NJ (US); Li Fan, Belle Mead, NJ (US); Jianzhong Qian, Princeton Junction, NJ (US); Xiaolan Zeng, Princeton, NJ (US)

(73) Assignee: Edda Technology, Inc., Princeton Junction, NJ (US)

( * ) Notice: Subject to any disclaimer, the term of this patent is extended or adjusted under 35 U.S.C. 154(b) by 943 days.

This patent is subject to a terminal disclaimer.

(21) Appl. No.: 11/647,597

(22) Filed: Dec. 29, 2006

(65) Prior Publication Data
US 2007/0192354 A1    Aug. 16, 2007

Related U.S. Application Data

(60) Provisional application No. 60/754,650, filed on Dec. 30, 2005.

(51) Int. Cl.
*G06F 3/00* (2006.01)
*G06F 9/44* (2006.01)
*G06F 9/445* (2006.01)
*G06F 9/46* (2006.01)

(52) U.S. Cl. .............. 719/313; 717/127; 717/164; 717/172; 717/177; 718/106

(58) Field of Classification Search ............... None
See application file for complete search history.

(56) References Cited

U.S. PATENT DOCUMENTS

2002/0180798 A1*  12/2002  Poor et al. ................. 345/781
2004/0003266 A1*  1/2004   Moshir et al. ............. 713/191

FOREIGN PATENT DOCUMENTS

| DE | 196 25 833 A 1 | 1/1998 |
|----|----|----|
| EP | 0 967 547 A2 | 12/1999 |
| EP | 1 445 914 A2 | 8/2004 |
| WO | WO 98/45793 | 10/1998 |
| WO | WO 2007/026318 A2 | 3/2007 |

OTHER PUBLICATIONS

International Search Report and Written Opinion of the International Searching Authority issued in International Application No. PCT/US2006/049476, dated Jul. 11, 2007.

* cited by examiner

*Primary Examiner*—Andy Ho
*Assistant Examiner*—Tuan Dao
(74) *Attorney, Agent, or Firm*—McDermott Will & Emery LLP

(57) ABSTRACT

A method and system is provided for data/process sharing. A decapsulating unit is provided and resides on first system where a first application system resides. The decapsulating unit monitors, on the first system, when encapsulated data from a second application system residing on a second system, is present in the first application system. The encapsulated data, once present on the first system, is decapsulated by the decapsulating unit to obtain a trigger corresponding to the second application system and encapsulated in the encapsulated data. The obtained trigger is analyzed and the second application system is launched on the first system based on the trigger.

25 Claims, 6 Drawing Sheets

METHODS AND SYSTEM FOR PROCESS SHARING AMONG INDEPENDENT SYSTEMS/APPLICATIONS VIA DATA ENCAPSULATION IN MEDICAL IMAGING

CROSS REFERENCE TO RELATED APPLICATION

This application claims priority under 35 U.S.C. §119 from Provisional Patent Application No. 60/754,650, filed on Dec. 30, 2005. The entire subject matter of the application is incorporated herein by reference.

BACKGROUND

1. Field of Invention

The present teaching relates generally to methods for process sharing in independent medical imaging, image communication, and image viewing systems/applications. Specifically, the present teaching relates to methods for process sharing and communication via encapsulation of a specified interactive analysis, processing, and viewing process into the image data.

2. Discussion of Related Art

With the large number of applications available on computing devices, there is a need to allow these applications to share with each other data created in different applications. One conventional solution is through a set of interfaces such as Object Linking and Embedding (OLE) developed by Microsoft. Such interfaces can be used to facilitate creating a compound document, in which objects or data from different applications reside in a single document and such object or data may be manipulated in an environment similar to its native environment in which the objects or data are initially generated. This is possible because an application may be embedded with an object or data it creates and imported as an integrated object into a document operated by a different application so that the application may be invoked to manipulate its object within the document when needed. For example, within a Microsoft Word document, one may incorporate a Microsoft Excel sheet embedded with the Microsoft Excel application. When the Word document is opened, one may invoke Microsoft Excel editing tool within the Word (for embedding) to process the incorporated Microsoft Excel spreadsheet.

In medical imaging, there is a similar need. A patient data processed in one application system such as a dedicated clinical application system (or a server based thereupon) may be imported into a different data processing environment and further being viewed and/or interactively manipulated using tools of the first application within the environment of the system to which the patient data is exported. As a specific example, a Computer-Aided Detection (CAD) system may process patient data to identify locations of suspicious regions for, e.g., tumors, and such identified locations may be exported, with possibly other associated data such as patient information and the original imaging data, to another medical imaging analysis application such as a Picture Achieving and Communication System (PACS) environment, which is physicians' routine reading environment. Within the PACS environment, the physicians may need to invoke the CAD application on the same patient data and to use the CAD system's interactive tools to further analyze the data. However, interactive tools available in the CAD system which may be used to interactively generate or edit markings of such suspicious locations are no longer available once the images are sent to the PACS environment.

Existing systems in medical imaging utilize certain commonly conformed standard in medical imaging such as Digital Imaging and Communication in Medicine (DICOM). To share images of different modalities, DICOM specifies how images should be stored and transferred. However, DICOM does not allow data to be embedded with application(s) that creates the data, making it difficult, if not impossible, to manipulate data created in one medical imaging system to be manipulated in its native environment in a different application system.

With the current technical limitations in medical imaging, to share the result data generated by an application among different medical imaging systems, there are two existing solutions. The first is simply sending the result data created in a first application to a second application in a recognizable format such as DICOM for display in the second application and for manipulation using tools of the second application. Under this solution, manipulating data by tools of the first application system in the environment of the second application system is not made possible. The second solution is to integrate the first application system such as CAD system with the second application system such as PACS through some mutually defined APIs. In this case, implementing the API-based integration requires code-level engineering effort, which can be not only time consuming but also cost inhibitive. For example, considering the complexity of CAD systems and PACS systems on today's market, the effort to achieve such API-based integration can be very costly. This kind of integration is especially difficult if one considers integration with systems already installed in a clinical environment. Other dedicated clinical applications, such as 3D visualization, have similar restrictions in their accessibility within another independent system.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

The present teaching is for process sharing and data communication among different independent medical processing systems via data encapsulation without common API or carrying out code-level integration between a plurality of systems.

Figure 1A:
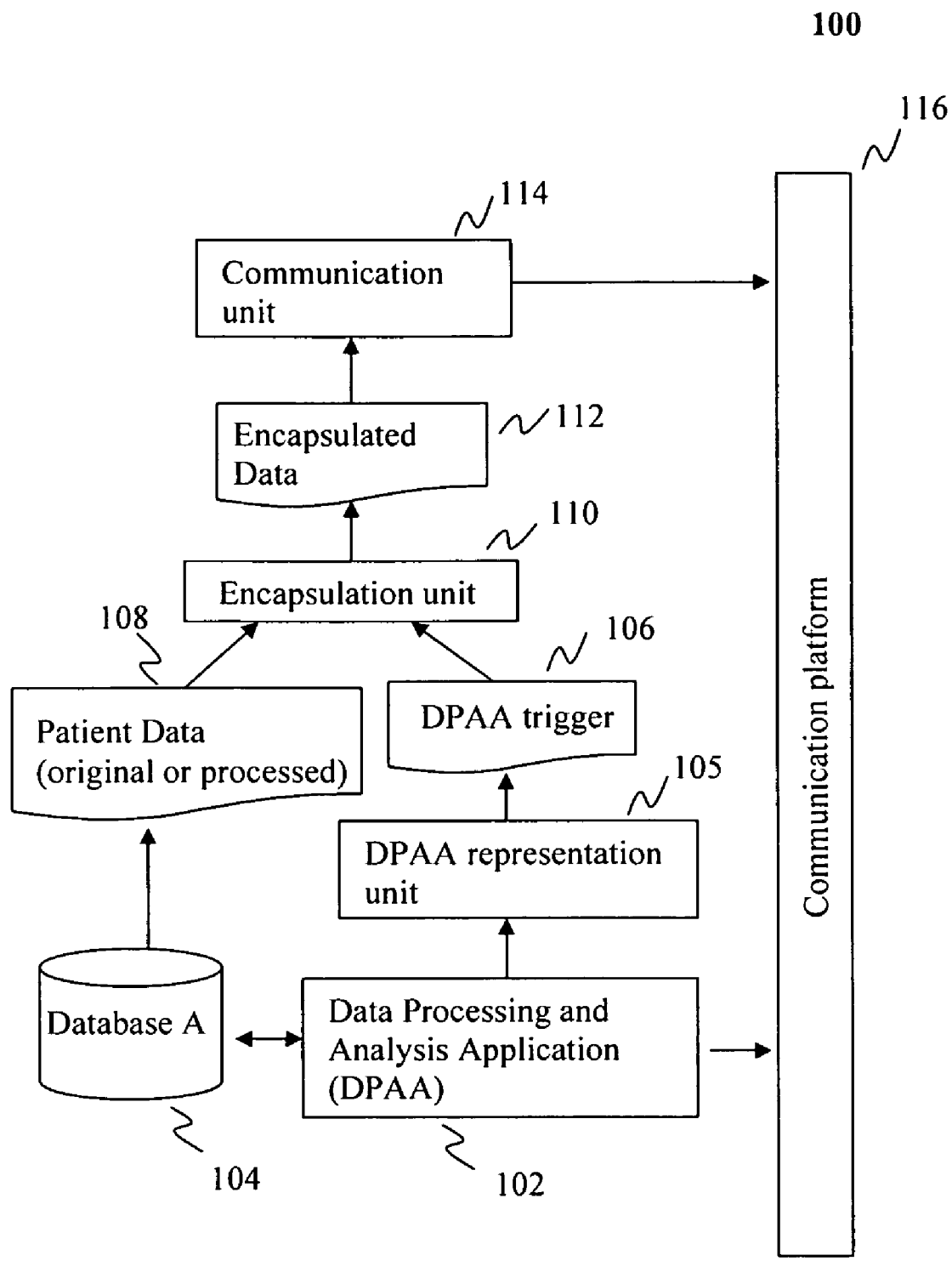
FIGS. 1a and 1b depicts an exemplary construct of a system diagram for process sharing between two independent systems/applications, according to an embodiment of the present teaching.
Figure 1B:
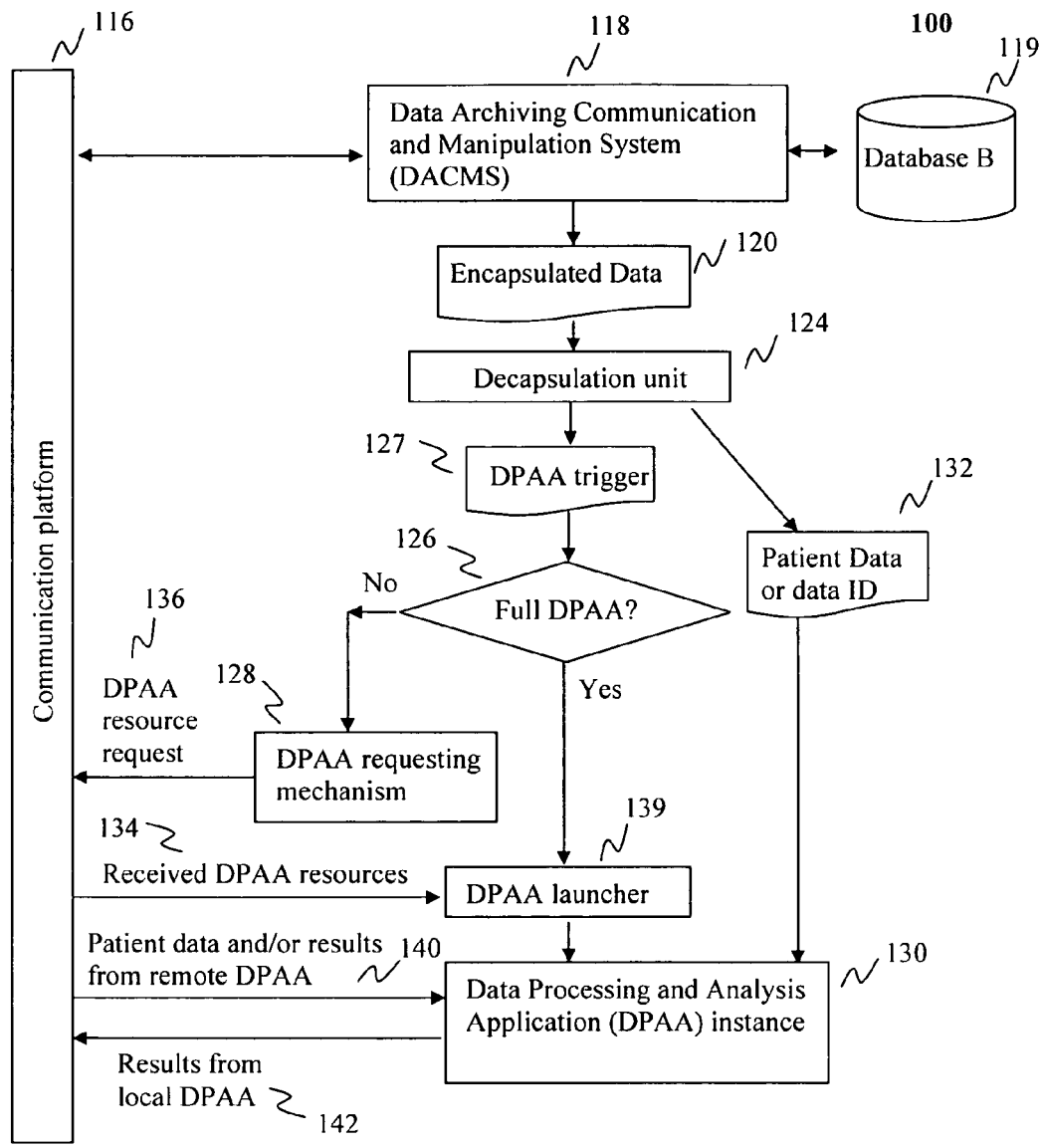

FIG. 1a and FIG. 1b shows an exemplary system diagram 100 facilitating process communication and data/process sharing, according to one embodiment of the current teaching. The system 100 involves two different applications, one is on the left of the communication platform 116 and the other is on the right of the communication platform 116. The two applications may or may not reside in separate computing devices. The system 100 comprises a Data Processing and Analysis Application (DPAA) unit 102, a DPAA representation unit 105, an encapsulation unit 110, a communication unit 114, a communication platform 116, and additionally all the parts residing on the second system, including a Data Archiving Communication and Manipulation System (DACMS) 118, a decapsulation unit 124, a DPAA requesting mechanism 128, a DPAA launching unit 139, which creates an instance of DPAA 130.

The DPAA 102 may process patient data from a data storage Database A 104. The Database A 104 may store both original patient data and processed result data. It may store data of different types, including, but not limited to, patient record, patient report, digital images, such as X-ray, CT, MRI, and results of data processing. The DPAA may be represented, through the DPAA representation unit 105, as a DPAA trigger 106. The DPAA trigger 106 may be in the form of a complete version of the DPAA application, a partial version of the DPAA application, or a symbolic representation of the DPAA such as an abstraction in the form of an identification number to be used to identify DPAA or a physical location representing where the DPAA is stored. When there are a plurality of application systems that are subject to encapsulation, each identification number may be defined to uniquely identify a specific application system. A DPAA trigger may also be a script specific to an application system which may be executed to launch the underlying application system.

The encapsulation unit 110 may be invoked, when data created by the underlying application system is to be exported to a different application system, to encapsulate the DPAA trigger 106 with patient data 108 and generate an encapsulated data 112. Since the DPAA trigger 106 may represent the underlying application system (DPAA) in different forms, the encapsulated data may embed, with patient data (original or processed), a complete or a partial version of the DPAA or simply a symbolic representation thereof. The encapsulated data may be exported via the communication unit 114 to the DACMS unit 118 via a communication platform 116. Standardized protocols such as DICOM may be used for exporting medical images.

The DACMS 118 may be any system or application that may perform certain functions, including, but not limited to, data storage, data communication, data processing, and data visualization. An example of such a system is a Picture Archiving and Communicating System (PACS). The DACMS 118 may store the encapsulating data into a data storage Database B, 119. If DPAA 102 and DACMS 118 are located in different computers, the communication platform 116 may be either a local area network (LAN), or a wide area network (WAN) or other types of communication media. If both DPAA 102 and DACMS 118 are located in the same computer, the communication platform 1116 may include, but not limited to, specific hard drive locations or a specific network port number.

The decapsulation unit 124 corresponds a functional block of the first application system such as the illustrated DPAA application system. However, the decapsulation unit 124 resides within a foreign environment of the second application system such as the DACMS system. Once being deployed on the second system, the decapsulating unit 124 monitors when an encapsulated object is imported from the first application system (e.g., DPAA) into the foreign environment (e.g., DACMS). When the decapsulation unit 124 detects that there is an encapsulated data is present in the second application system, the decapsulation unit 124 may decapsulate the encapsulated data and extract both the encapsulated DPAA trigger 127 and the patient data or data ID 132 from the encapsulating data 120.

The decapsulation unit 124 may need to be pre-loaded into the environment of DACMS, prior to the second application system such as DACMS starts to import encapsulated data from the first application system such as DPAA. The deployment of the decapsulation unit 124 is through either direct installation, or a download or deployment from DPAA 102. At 126, as shown in FIG. 1b, it is determined if the DPAA trigger represents a full or a partial version of the DPPA. If the DPPA trigger is a full DPAA package, a DPAA instance 130 may be instantiated and launched in the environment of the DACMS 118 by the DPAA launcher 139. If the DPAA trigger represents a partial DPPA or a symbolic representation such as an indicator of the DPAA, e.g., the location where DPAA is stored, the DPAA requesting mechanism 128 may send a DPAA resource request 136 to the communication platform 116. The received DPAA resources 134 may then be used to instantiate an instance of the DPAA and the DPAA launcher 139 may then launch the created instance of DPAA 130 in the DACMS environment.

The DPAA launcher 139 may correspond to the DACMS, which may be in conformance with a pre-defined protocol. The DPAA launcher 139 may also be an independent program running in the backend in the DACMS environment. When an instance of DPAA 130 is launched, the activated DPAA instance may be used to manipulate the patient data from the first application system or DPAA. If additional results were generated by the original first DPAA, the launched DPAA in the foreign environment may send a request for the results to be sent to the launched DPAA 130. The communications between the original DPAA and the launched DPAA in the foreign environment may be based on the patient data ID 132.

On the other hand, if some information needed by the launched DPAA is not present in the decapsulated data 132, the launched DPAA may request such information from either the original DPAA 102 residing on the first system or from DACMS 118 through some standard interfaces, such as DICOM. In this way, both DACMS and DPAA can operate on the same patient data. The processed results 142 from the launched DPAA may be sent to DACMS 118 and remote DPAA 102 via the communication platform 116.

Figure 2:
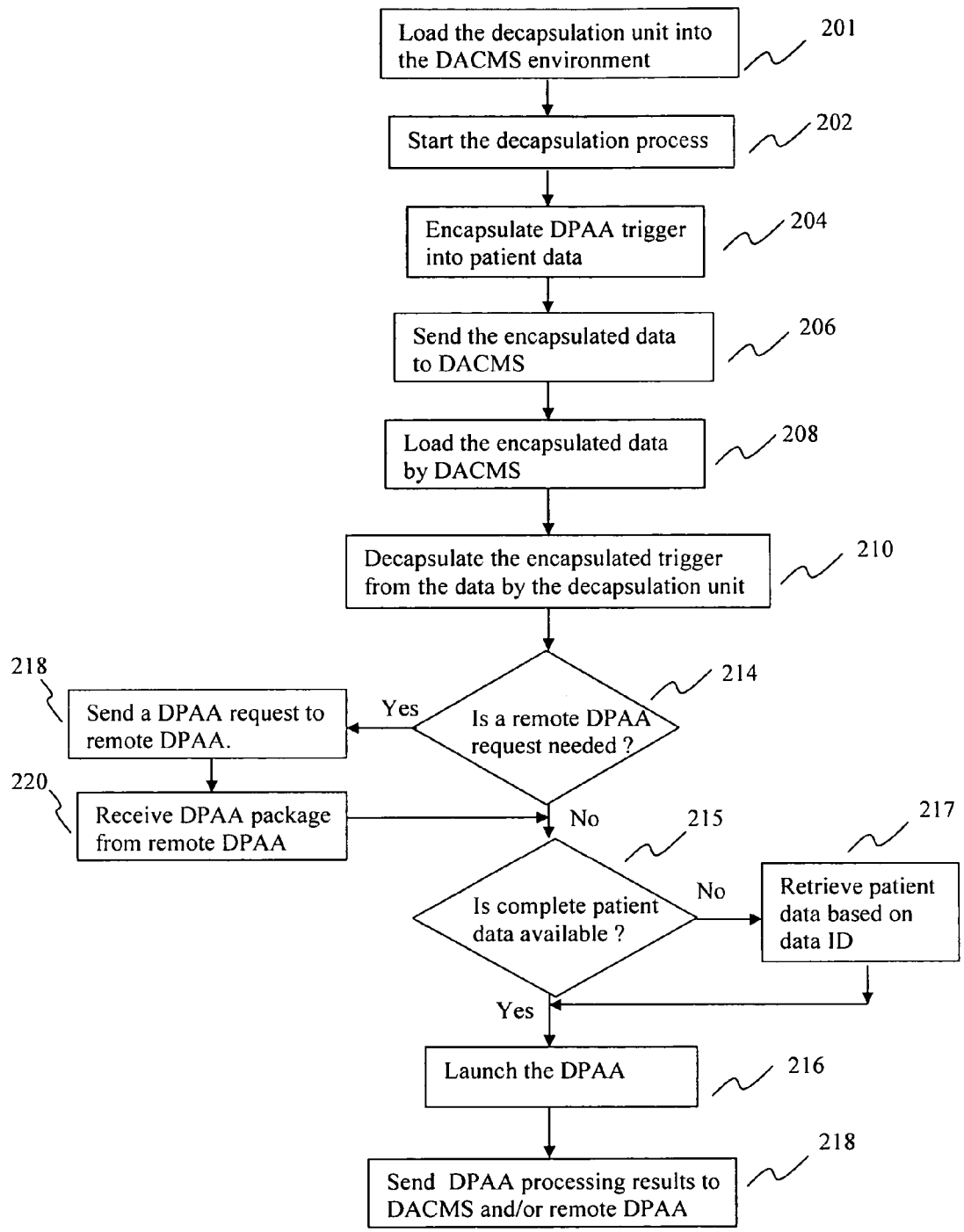
FIG. 2 shows a flowchart of process communication and process sharing between multiple systems/applications, according to an embodiment of the present teaching.

FIG. 2 illustrate an exemplary workflow of the system 100, according to one embodiment of the present teaching. At step 201, the decapsulating unit 124 may be first deployed into the DACMS environment, either remotely from the DPAA environment or through local installation. Once deployed in the DACMS environment, the decapsulation unit may then start to monitor when an encapsulated object created by a DPAA system is imported into the DACMS environment. It may constantly check for the existence of a DPAA trigger, according to the encapsulation rule of the encapsulation unit. Such checking may be performed within a memory, in which the DACMS program may reside and operate. In some embodiment, such checking may be performed throughout the memory. In other embodiments, such check may be performed at certain locations of the memory. In yet other embodiments, such check may be performed in some known locations of the memory where the DACMS system stores relevant information.

After the decapsulation unit 124 is deployed in a foreign environment, the process/data sharing may be facilitated in the following steps. At step 204, the encapsulation unit may encapsulate the DPAA trigger 106 into the patient data 108. At step 206, the encapsulated data may be sent to the DACMS 118 by the communication unit 114. The encapsulated data may be loaded or opened for viewing or other operations by DACMS, at step 208. Once the data is within the DACMS environment, the decapsulation unit 124 detects its presence and then decapsulates the imported encapsulated data, e.g., by a process running on the backend in DACMS environment, to separate the DPAA trigger, at step 210. At step 214, it is determined whether a full or a partial version of the DPAA is encapsulated in the trigger. If a full version of the DPAA is not encapsulated, a request may be sent to the original DPAA. If the original DPAA 102 responds to the request, a request for retrieving DPAA resources is sent from the original DPAA 102 at step 218.

Through such communications, the requested DPAA resources may be received at step 220. At step 215, it is determined whether the decapsulated data contains the complete patient data. If not, the patient data may be retrieved from the remote DPAA 102, based on the data ID, at step 217. After both DPAA components and the patient data are available, a DPAA instance may be instantiated and launched at step 216. At step 218, the processed results from the launched DPAA may be back sent to DACMS or to the original DPAA.

Figure 3A:
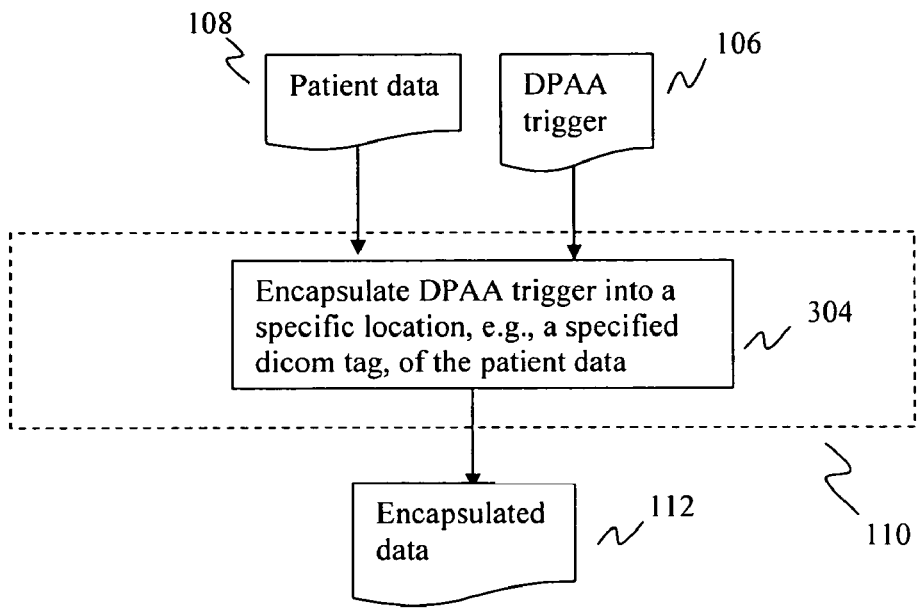
FIG. 3a is an exemplary flowchart for data encapsulation by encapsulating a location of an application with data created by the application, according to an embodiment of the present teaching.

FIG. 3*a* shows an exemplary embodiment of the encapsulation unit 110, according to the present teaching. The encapsulation unit 110 may take as input a patient data 108 and a DPAA trigger 106. At step 304, the DPAA trigger may be encapsulated into the patient data 108 by embedding the DPAA trigger into a specific location in the patient data. An exemplary embodiment is to embed the DPAA trigger into a DICOM tag of the patient data.

Figure 3B:
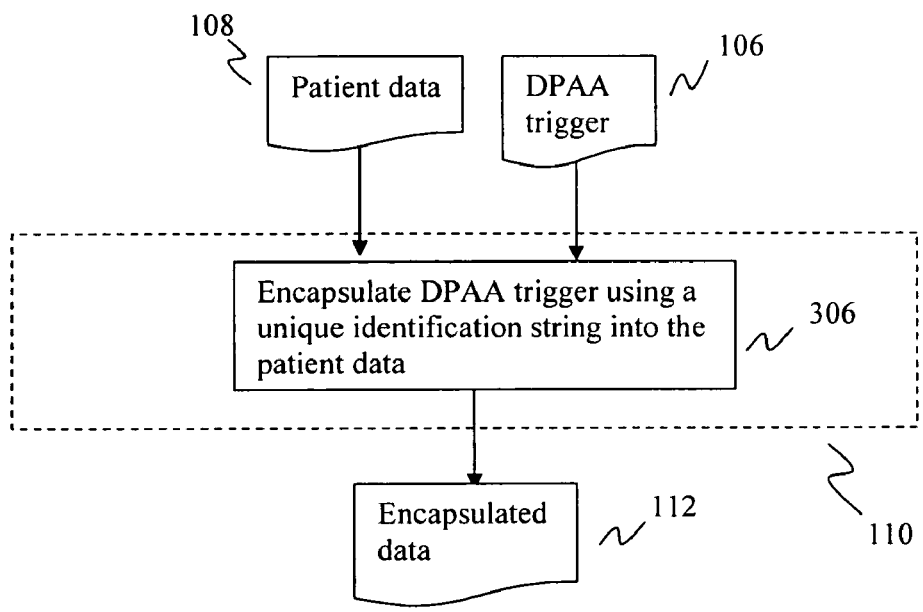
FIG. 3b is another exemplary flowchart for data encapsulation by encapsulating an identification string of an application with data created by the application, according to an embodiment of the present teaching.

Another exemplary embodiment of the encapsulation unit 110 is shown in FIG. 3*b*. At step 306, the DPAA trigger 302 may be combined with a unique identification string to form a string-identifiable DPAA trigger. The identification string may be used later to identify the location of the encapsulated information. The string-identifiable DPAA trigger may then be embedded into the patient data. One embodiment of such encapsulation is to put the string-identifiable DPAA trigger into the pixel data of the patient image. For example, it may be put into the corner pixels of the image, so that no diagnostic information may be lost.

The encapsulation unit 110 may keep all other information in the input patient data intact. For example, the patient name and patient ID of a DICOM image may remain the same. The encapsulation unit 110 may also only keep necessary information needed to identify the patient data, such as the patient name and patient ID and the ImageInstanceUID in the DICOM header of the data. In either case, the encapsulated data may be organized under the same patient into the data storage unit 120 by the DACMS 118, according to the DICOM protocol.

Figure 4A:
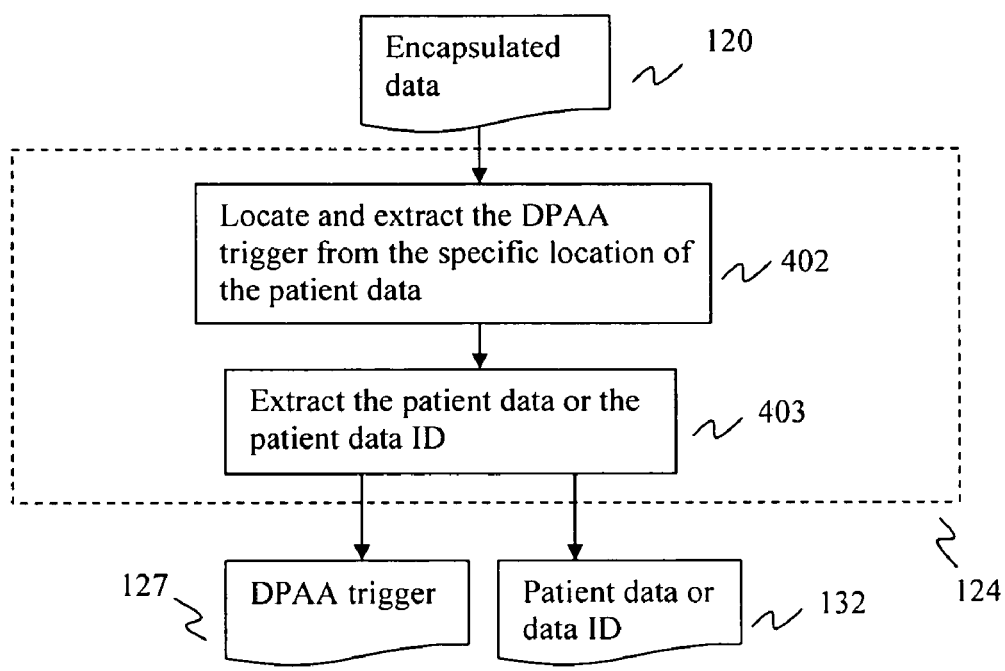
FIG. 4a is an exemplary flowchart for data decapsulation by decapsulating a location of an application from data created by the application, according to an embodiment of the present teaching.

FIG. 4*a* depicts an exemplary embodiment of the decapsulation unit 124, corresponding to the embodiment of encapsulation in FIG. 3*a*. The decapsulation unit 124 takes the encapsulated data 120 as input. At step 402, the decapsulation unit 124 may extract the encapsulated DPAA trigger, from the pre-defined location, chosen at step 304, of the encapsulated data 120. At step 403, the patient data or data ID may be extracted.

Figure 4B:
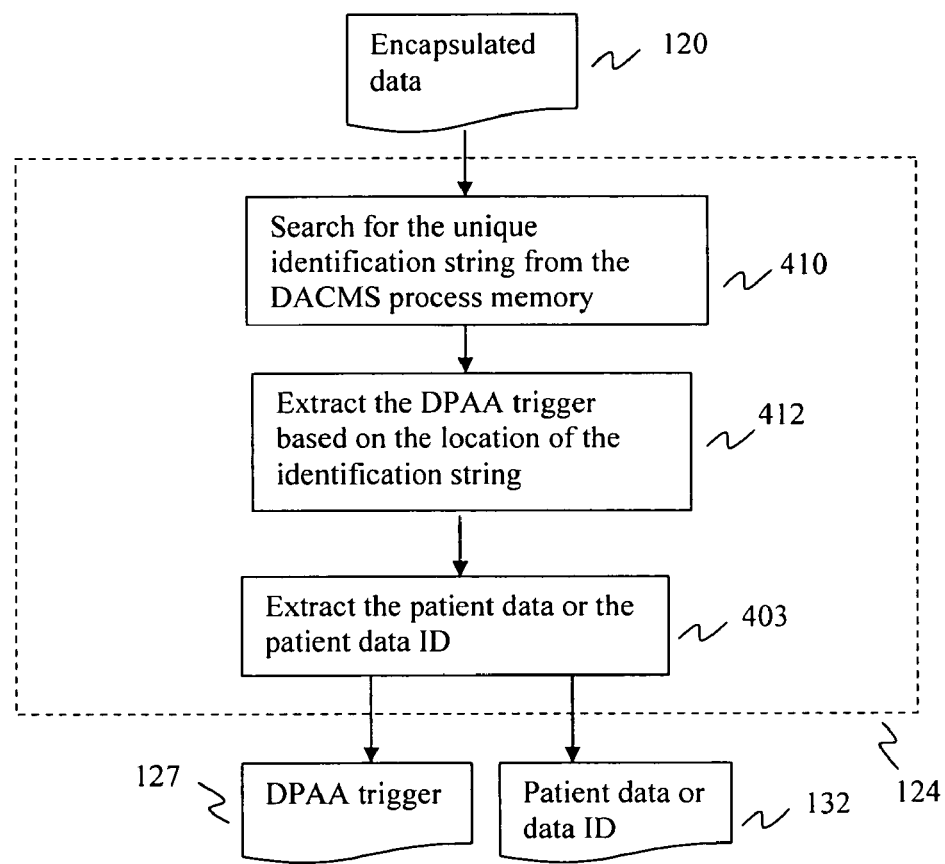
FIG. 4b is another exemplary flowchart for data decapsulation by decapsulating an identification string associated with an application from data created by the application, according to an embodiment of the present teaching.

FIG. 4*b* shows another exemplary embodiment of the decapsulation unit 124, corresponding to the embodiment of encapsulation in FIG. 3*b*. At step 410, the decapsulation unit 124 may search for the unique identification string, chosen at step 306. One embodiment is to search for the unique identification string in the process memory of the DACMS, based on program name. After the unique identification string is found, the encapsulated DPAA trigger may then be extracted, at step 412. One embodiment is to read certain bytes of data following the unique identification string. At step 403, the patient data or data ID may be extracted.

While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A method implemented on a first computer system having a processor, a storage, and a communication platform capable of connecting to a network for sharing data with a second computer system, comprising:

uploading a decapsulating unit on the first computer system where a first application resides;

automatically monitoring, by the decapsulating unit on the first computer system, a presence of encapsulated data, originated from a second application residing on the second computer system, wherein the decapsulating unit does not open a file storing the encapsulated data, the first application does not communicate with the decapsulating unit and the second application, and the presence of the encapsulated data is detected only after the file is opened by the first application on the first computer system;

recognizing, by the decapsulating unit, a trigger encapsulated in the opened file storing the encapsulated data, wherein the trigger provides information in association with the second application;

analyzing the trigger; and launching the second application on the first computer system based on the trigger.

2. The method according to claim 1, wherein the decapsulating unit is installed on the first system.

3. The method according to claim 1, wherein the decapsulating unit is downloaded or deployed from the second system to the first system.

4. The method according to claim 1, wherein the decapsulating unit is provided by a third system.

5. The method according to claim 1, wherein the trigger represents one of a full version of the second application system, a partial version of the second application system, an identifier corresponding to the second application system that is recognizable on the second system, and a location indicator corresponding to where the second application system resides on the second system.

6. The method according to claim 1, wherein the launching the second application system, when trigger contains a full version of the second application system, comprises:
instantiating an instance of the second application system on the first system; and
launching the instance of the second application system on the first system.

7. The method according to claim 1, wherein the launching the second application system, when the trigger represents a partial version of the second application system, comprises
sending a resource request to the second system for a full version of the second application system based on the trigger;
receiving a request to receive the requested full version of the second application system;
instantiating an instance of the second application system on the first system; and
launching the instance of the second application system on the first system.

8. The method according to claim 1, further comprising encapsulating, on the second system, data from the second application system and the trigger to generate the encapsulated data.

9. The method according to claim 8, wherein the encapsulating comprises embedding the trigger into a pre-defined location of the data.

10. The method according to claim 8, wherein the encapsulating comprises employing an identification string as the trigger in the data.

11. The method according to claim 1, wherein the decapsulating comprises:
identifying a pre-defined location of the data;
extracting the trigger from the pre-defined location of the data.

12. The method according to claim 1, wherein the decapsulating comprises:
searching for a location in the data where an identification string corresponding to the second application system is stored;
retrieving the trigger from the location with the identification string.

13. The method according to claim 1, wherein the first system and the second system correspond to a same computing system.

14. A system for data sharing, comprising
a first application residing on a first computer system;
a second application residing on a second computer system;
a decapsulating unit loaded on the first computer system configured to automatically monitor a presence of encapsulated data originated from the second application wherein the decapsulating unit does not open a file storing the encapsulated data, the first application does not communicate with the decapsulating unit and the second application, and the presence of the encapsulated data is detected only after the file is opened by the first application on the first system, and
recognize a trigger encapsulated in the opened file storing the encapsulated data, wherein the trigger provides information in association with the second application;
a launcher residing on the first computer system configured to launch the second application on the first computer system based on the trigger after the decapsulating unit detects recognizes the trigger.

15. The system according to claim 14, wherein the decapsulating unit is installed on the first system.

16. The system according to claim 14, wherein the decapsulating unit is downloaded or deployed from the second system to the first system.

17. The system according to claim 14, wherein the decapsulating unit is provided by a third system.

18. The system according to claim 14, wherein the encapsulating unit embeds the trigger into a pre-defined location of the data.

19. The system according to claim 14, wherein the encapsulating unit employs an identification string as the trigger to be stored in the data.

20. The system according to claim 14, wherein the decapsulating unit:
identifies a pre-defined location of the data;
extracts the trigger from the pre-defined location of the data.

21. The system according to claim 14, wherein the decapsulating unit:
searches for a location in the data where an identification string corresponding to the second application system is stored; and
retrieves the trigger from the location with the identification string.

22. The system according to claim 14, wherein the first system and the second system correspond to a same computing system.

23. The system according to claim 14, wherein the trigger represents one of a full version of the second application system, a partial version of the second application system, an identifier corresponding to the second application system that is recognizable on the second system, and an location indicator corresponding to where the second application system resides on the second system.

24. The system according to claim 14, further comprising a requesting mechanism residing on the first system, wherein the requesting mechanism sends a request to the second system to obtain resources relating to the second application system when the trigger does not include a full version of the second application system.

25. The system according to claim 24, wherein the requesting mechanism sends a request to the second system to obtain information that is not present in the encapsulated data.

* * * * *